United States Patent [19]

Park

[11] Patent Number: 5,255,399
[45] Date of Patent: Oct. 26, 1993

[54] FAR INFRARED RAYS SAUNA BATH ASSEMBLY

[76] Inventor: Hun C. Park, 923-35 Gyeisan-dong, Puk-gu, Inchun, Rep. of Korea

[21] Appl. No.: 812,448

[22] Filed: Dec. 23, 1991

[30] Foreign Application Priority Data

Dec. 31, 1990 [KR] Rep. of Korea ............ 22740/1990

[51] Int. Cl.⁵ ............................................ A61H 33/06
[52] U.S. Cl. ......................................... 4/525; 4/524; 4/605
[58] Field of Search .................. 4/524, 525, 605, 612, 4/613, 614

[56] References Cited

U.S. PATENT DOCUMENTS

| | | | |
|---|---|---|---|
| 1,765,915 | 6/1930 | Haase | 4/628 X |
| 3,007,178 | 11/1961 | Altman et al. | 4/525 |
| 3,396,411 | 8/1968 | Vieceli | 4/525 |
| 4,044,772 | 8/1977 | Schloss | 4/524 X |
| 4,340,981 | 7/1982 | Vanags | 4/525 X |
| 4,432,103 | 2/1984 | Hunziker | 4/525 |
| 4,833,739 | 5/1989 | Sakakibara et al. | 4/524 |

FOREIGN PATENT DOCUMENTS

| | | | |
|---|---|---|---|
| 0300577 | 1/1989 | European Pat. Off. | 4/524 |
| 3911679 | 10/1990 | Fed. Rep. of Germany | 4/524 |
| 2195530 | 4/1988 | United Kingdom | 4/524 |

*Primary Examiner*—Henry J. Recla
*Assistant Examiner*—Robert M. Fetsuga
*Attorney, Agent, or Firm*—Lowe, Price, LeBlanc & Becker

[57] ABSTRACT

A far infrared rays sauna bath assembly includes a small prefabricated construction assembly for easy carrying and construction and several ceramic plane surface exothermic heaters having a very thin thickness about 1 mm of which occupy a minimum area when mounted and provide further radiation available for a large evenly radiation heating with an effective heat ratio. A height controlling shower machine is available to control the height for a user. An air dryer for full body drying a finger pressure cushion palette having multiple protrusions for finger pressure therapy and a discharge for bottom drain water are included. An air discharge door for steam venting and heat control, a stereo music amplifier and cassette and a golden (coin inlet) timer for business charges may also be provided.

6 Claims, 6 Drawing Sheets

FAR INFRARED RAYS SAUNA BATH ASSEMBLY

TECHNICAL FIELD

The present invention relates to a far infrared rays sauna bath assembly, and particularly, to a small assembly type far infrared rays sauna bath for one man use.

BACKGROUND ART

A number of conventional sauna baths have been proposed with a public bath tub.

These types have been proposed in Korean patent publication No. 690/86 and Korean Utility Model Publication No. 1296/88.

In the conventional prior art baths, however, their function was limited as sauna baths only.

Thus, ancillary shower and attendant facilitates were required so that the equipment costs were excessive.

In the conventional baths, a far infrared rays rod heater is arranged at the top end of the equipment. Therefore, radiation to all of body of the user was not possible and thermal efficiency was not efficient.

Furthermore, the applying of far infrared rays rod heater results in electric leakage and equipment defects in the steam sauna. In addition, steam produced from the steam heater changes to water drops and flows to the lower vessel which is too small to drain water. The water inlet for the steam heater also causes problems. The thermal blower of the lower end of the container was used to drying for the laundry only. The steam of the inner space of the container causes additional problems.

SUMMARY OF THE INVENTION

It is, therefore, one object of the present invention to solve the aforementioned problems of the prior art.

The present invention provides a far infrared rays sauna with a small prefabricated box type assembly for easy carrying and construction.

Further, the present invention provides a far infrared rays sauna bath with shower, drying and an all body sauna.

The far infrared rays sauna assembly according to the present invention comprises a number of ceramic plate exothermic heaters, an air dryer, a stereo amplifier and cassette, an instant thermal water supplier, a control box, a golden (coin inlet) timer and a finger pressure therapy cushion palette with a box-like prefabricated construction.

Additional objects and features of the present invention will be apparent from the following description, in which reference is made to the accompanying drawings.

DETAILED DESCRIPTION OF THE PREFERRED EMBODIMENT

Figure 1:
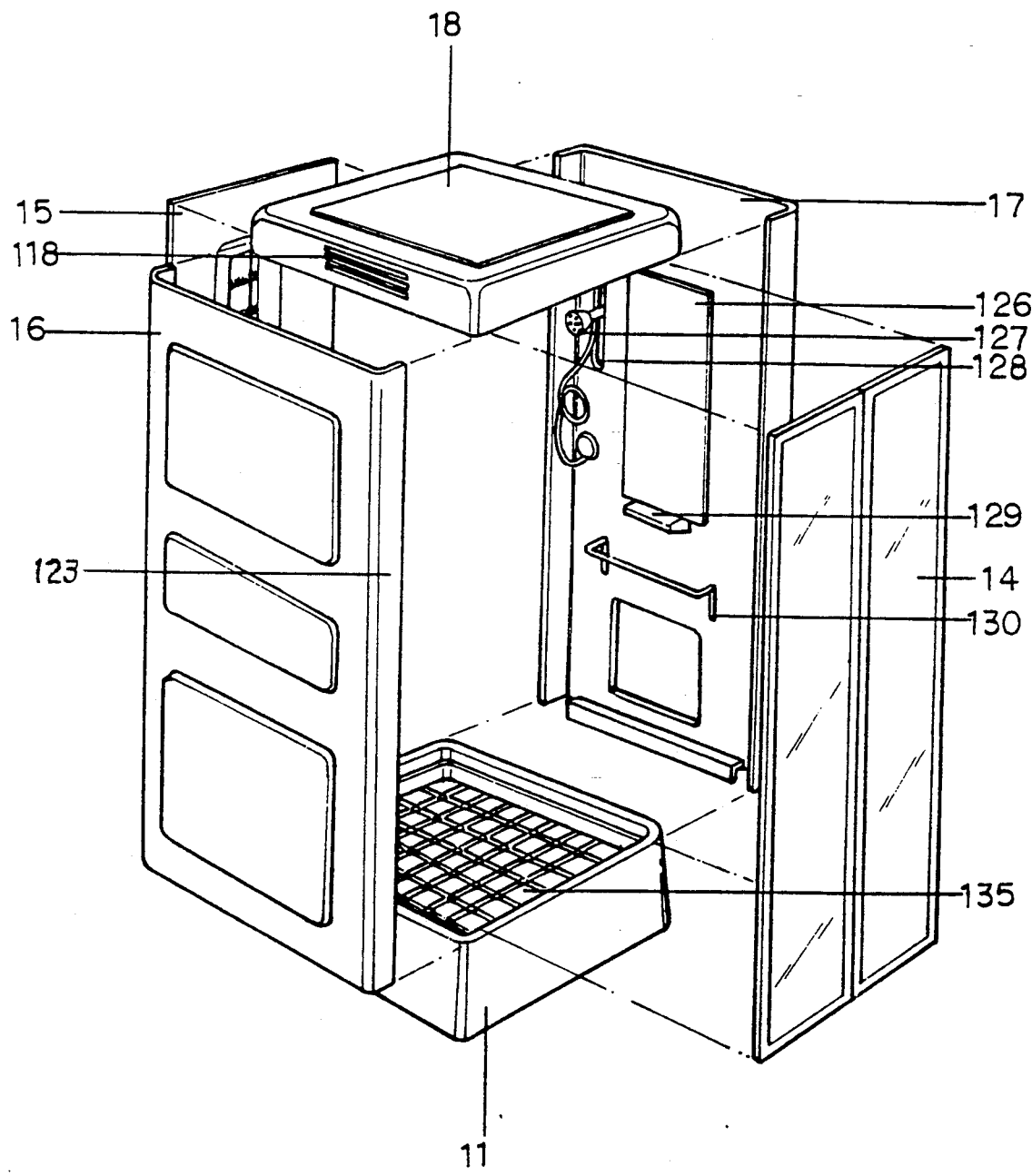
FIG. 1 is an exploded perspective view of the far infrared rays sauna assembly of a preferred embodiment of the present invention.
Figure 2:
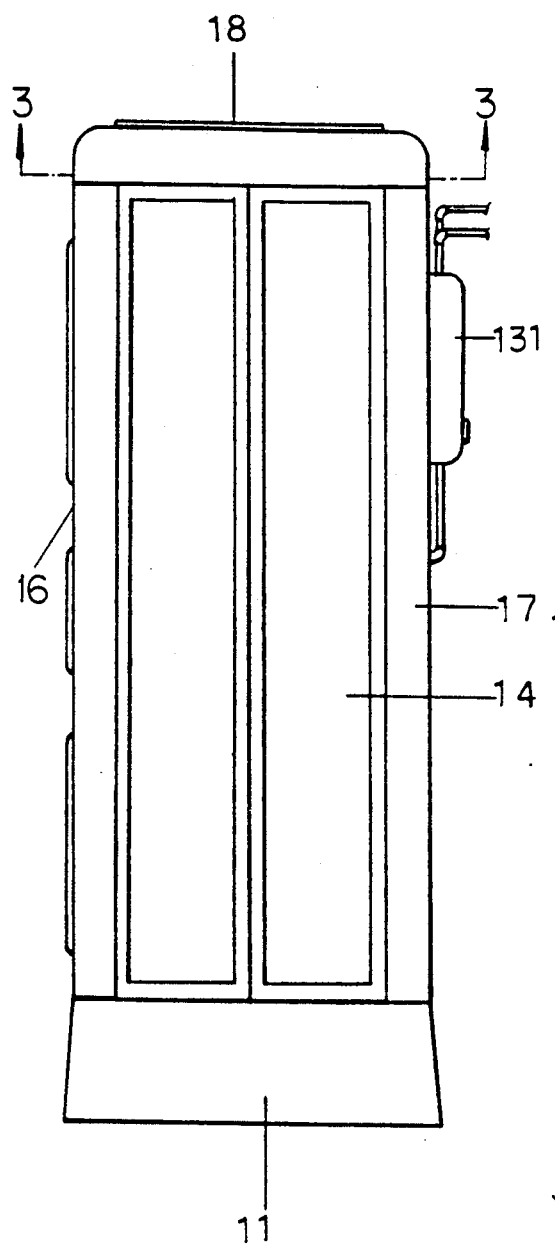
FIG. 2 is a front view of the far infrared rays sauna assembly of a preferred embodiment of the present invention.

Referring now to the figures of the drawings, and in particular to FIG. 1, a far infrared rays sauna bath assembly according to the present invention comprises; a lower body 11 shaped as a vessel having a drainage 12 on a side of the bottom, and a drain hose 13 for the drain water to the outlet.

Figure 6:
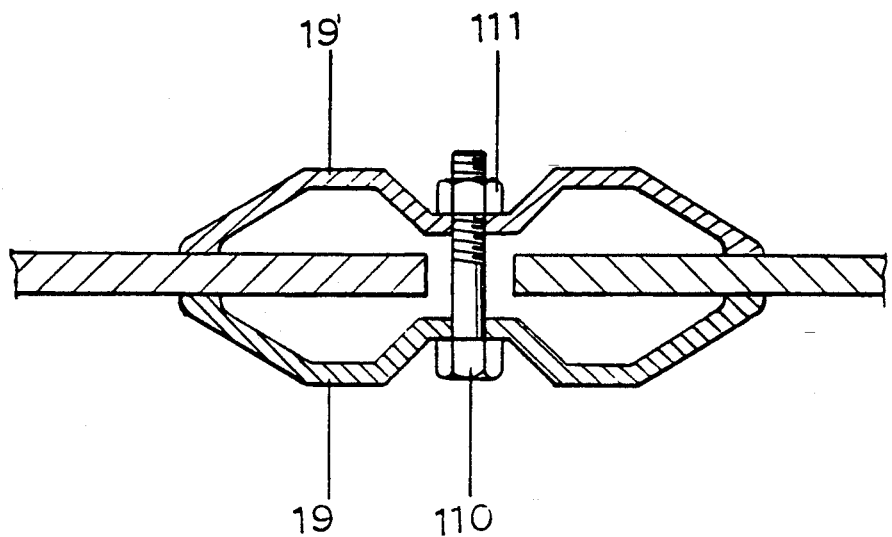
FIG. 6 is a plan section view of the cover plate joint according to the present invention.

A pair of doors 14, a back cover plate 15 and side cover plates 16, 17 are mounted on the upper front and back sides, and both sides of the lower body 11. An upper cover body 18 is joined twice on the upper side of the lower body 11, forming a box like container. The joint of the cover plates of the above mentioned surface and sides is shown in FIG. 6.

The joining bodies 19 and 19' are joined on the back and front side of joining portions of the adjacent plates by bolt 110 and nut 111 at several points of the sides of the plates.

Figure 8:
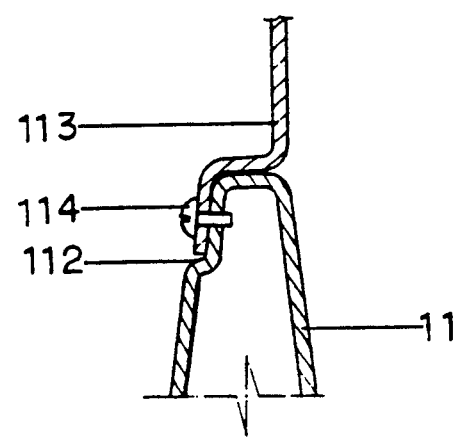
FIG. 8 is a partly diagrammatic sectional view of the lower portion cover plate joint according to the present invention.

In FIG. 8, the lower body 11 is joined by jointing nut 114 connecting junction part 112 on the upper side of the inner periphery of lower body 11 and inward folding end 113 of cover plate lower end. Water droplets from the inside bottom do not leak to the outside with this construction.

Figure 7:
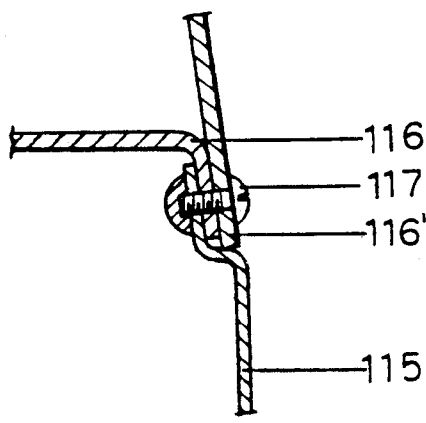
FIG. 7 is a partly diagrammatic sectional view of the upper cover part joint according to the present invention.

In FIG. 7, the upper cover body 18 assembly attaches to inwardly folding junction part 115 formed on the upper end of each cover plate. The inside and outside end parts 116 and 116' of the double upper cover body 18 are mounted on the outside and then fixed by jointing nut 117. Thus, a small prefabricated box type assembly for easy carrying and construction for a far infrared rays sauna tub is constructed.

Figure 3:
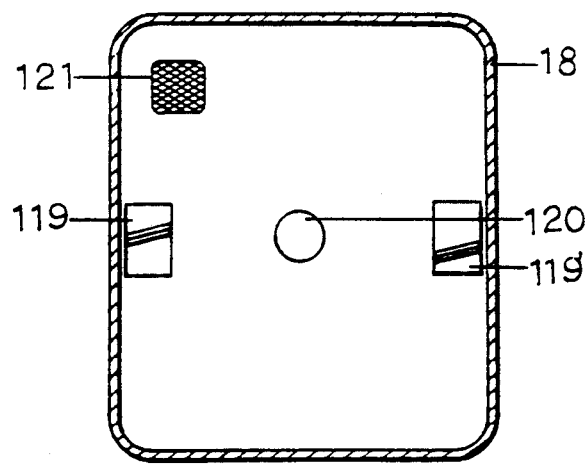
FIG. 3 is a cross sectional view along the A-A line of FIG. 2.
Figure 4:
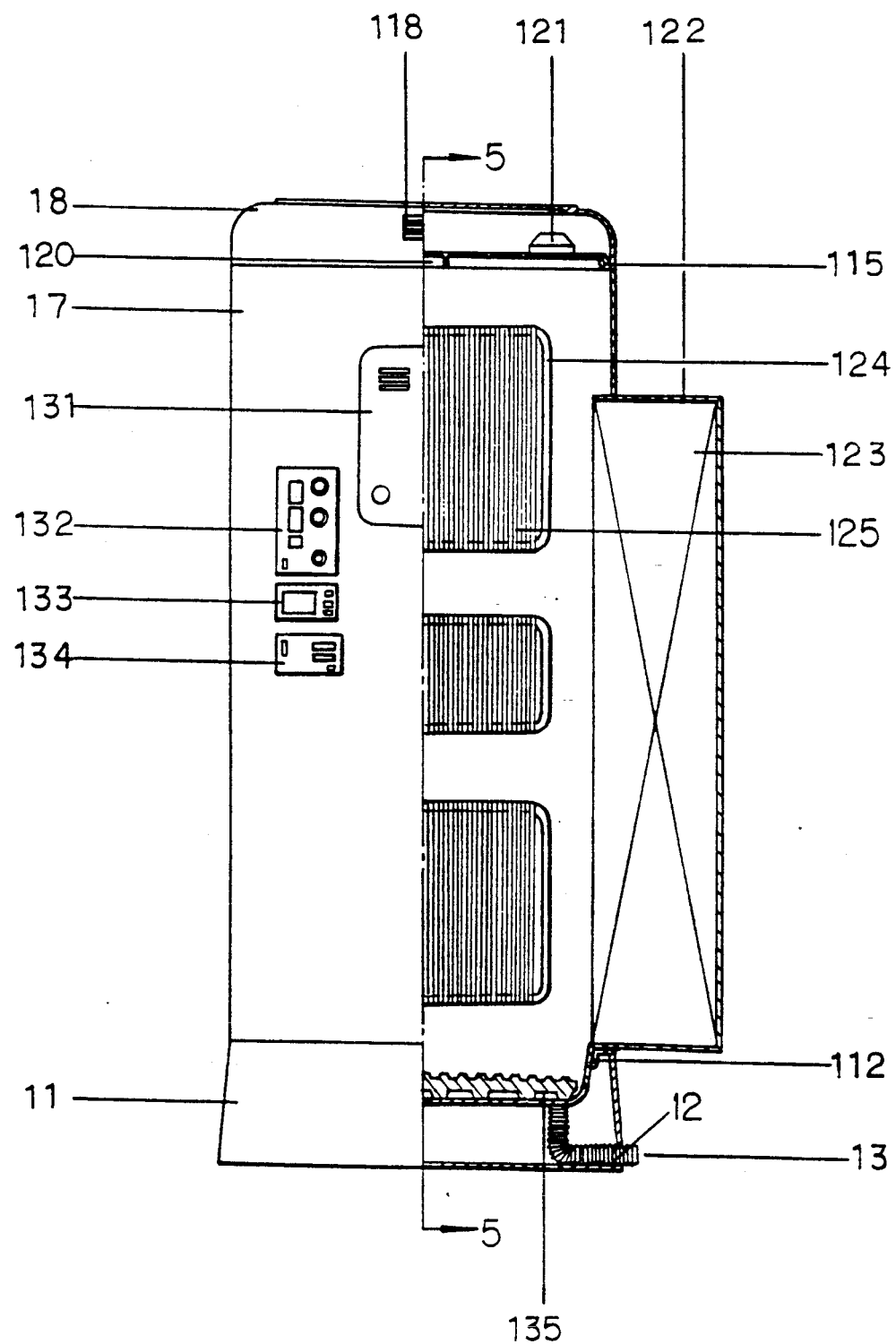
FIG. 4 is a right half partly sectional view of the far infrared rays sauna assembly of a preferred embodiment of the present invention.
Figure 5:
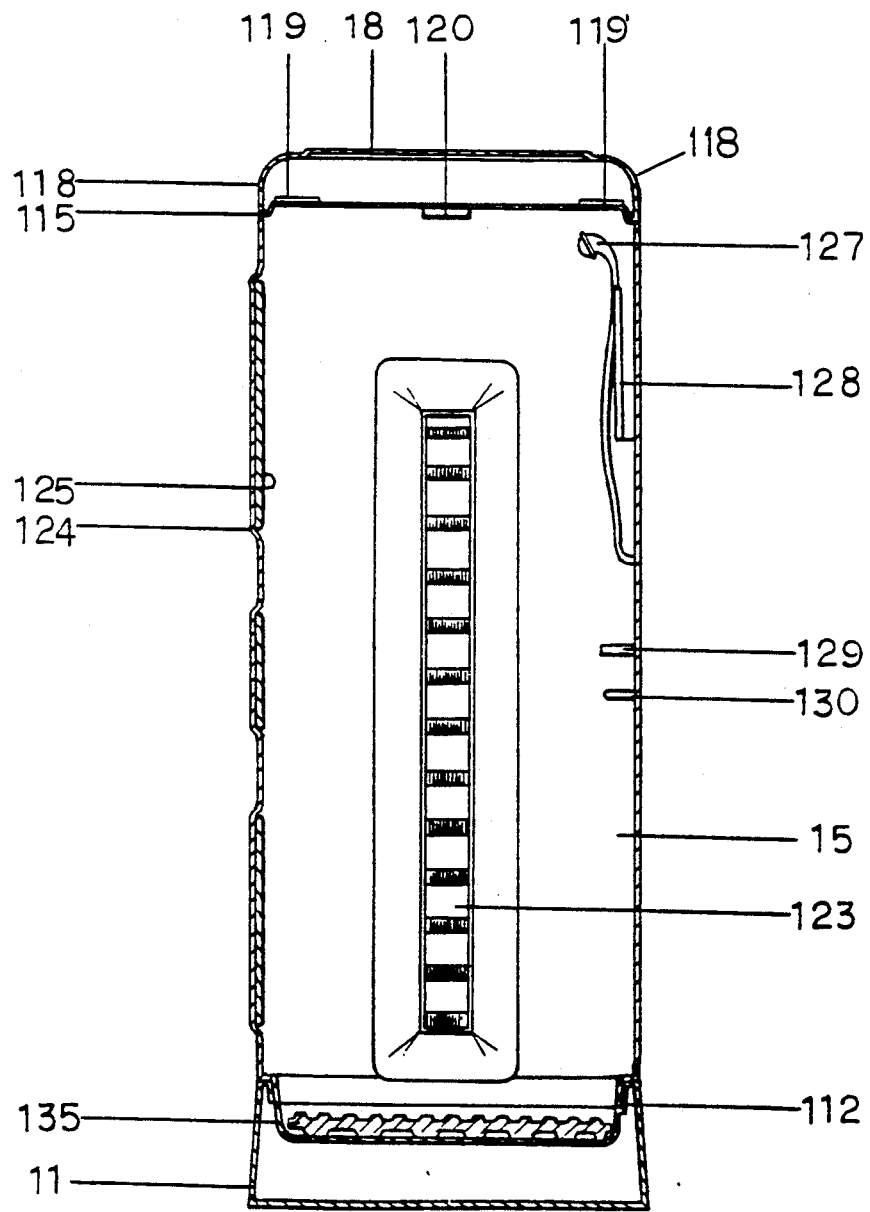
FIG. 5 is a cross sectional view along the B—B line of FIG. 4.

With reference to FIGS. 3–5, air discharge holes 118 are formed at both sides of the double covered upper cover body 18. Then, steam from the close controlling air discharge doors 119 and 119' installed at both sides of the inner overhead can discharge air outwardly. A light lamp 120 and stereo amplifier 121 are disposed at the center and one side of the overhead, respectively. An air dryer 123 is mounted on the inner portion of a concave body 122 formed at the center part of back surface cover plate 15. A number of ceramic plate exothermic heaters 125 are disposed on the concave portion 124 and on the inside of protrusion formed points on the left side cover plate 16.

The thickness of each ceramic plate exothermic heater 125 is about 1 mm, thus the heating unit accordingly to the present invention provides maximum heating thermal radiation area evenly with a thin and small area heater. A mirror 126, a soap tray 129, a hanger 130 and a shower unit 127 having a height control means 128 are installed on the right side cover plate 17, respectively. The shower unit 127 can produce a massage shower, purifying water shower, jet shower or fog shower.

A controlling box unit 132 controls the automatic thermal control function, timer control function, light lamp control function, leakage break function, melody function, music box function and water supplier 131. The instant thermal water supplier 131 to the shower 127 is mounted on the outside of the cover plate 17. The stereo cassette 133 and golden timer 134 for coin inlet charge are also mounted on the outside of the cover plate 17.

A finger pressure therapy cushion palette 135 is installed for water discharge easily and finger pressure therapy to the sole of a foot.

Figure 9:
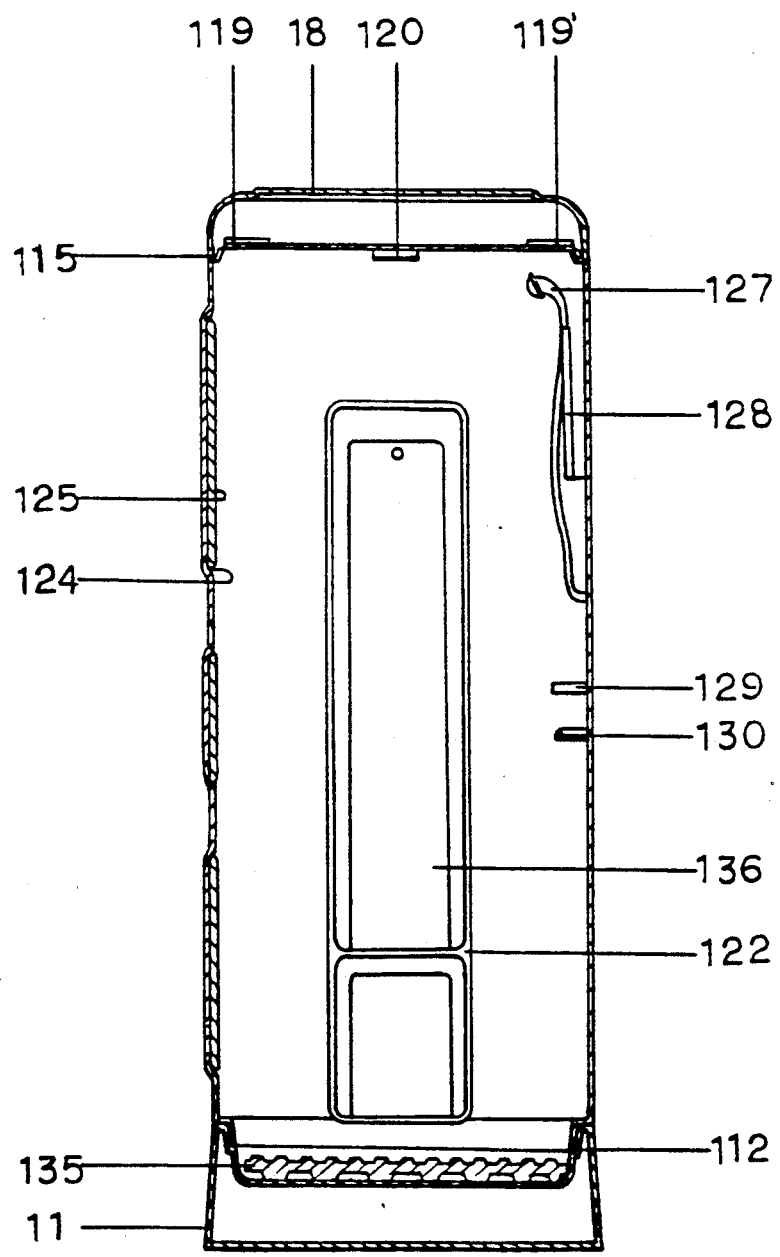
FIG. 9 is a cross section view along the B—B lines of FIG. 4 as an another embodiment of the present invention.

In FIG. 9, and as an another embodiment of the present invention, an inside wardrobe 136 is provided in substitution for the air dryer 123 mounted on the inner portion of a concave body 122 formed at the center part of a back surface cover plate 15.

As mentioned above, a far infrared rays sauna bath assembly according to the present invention comprises; a small prefabricated construction assembly for easy carrying and construction which includes several ceramic plane surface exothermic heaters having a very thin thickness of about 1 mm of which occupy a small area that provide a large even radiation to a full body of a user with an effective heat ratio. A height controlling shower machine 127 is available to control the height for the user. An air dryer for full body drying, a finger pressure cushion palette 135 having many protrusions for finger pressure therapy and a discharge for bottom drain water are also provided. An air discharge door for steam venting and heat control, a stereo music amplifier 121 and golden (coin inlet) timer 134 for business charges are also included.

I claim:

1. A far infrared rays sauna assembly having a small box type prefabricated construction comprising:
   a) a lower body supporting a well, each of said lower body and said well including a drain hole, each said drain hole connected by a drain hose, said lower body including a palette arranged in said well, said palette having a plurality of protrusions on an upper surface thereof, said lower body having a joining part extending along an upper periphery of said lower body;
   b) a back cover plate and a pair of doors;
   c) a left side cover plate and a right side cover plate, each said left side cover plate, said right side cover plate and said back cover plate having a folded lower bottom for connection to said joining part of said lower body using joining nuts;
   d) a plurality of joining bodies for connecting together adjacent edges of each of said back cover plate, left side cover plate and right side cover plate;
   e) an upper body, said upper body forming a chamber and having double wall construction along a lower peripheral edge for attachment to upper edges of at least said back cover plate and said left side and said right side cover plates, said upper body, said lower body, said back cover plate and said left side and said right side cover plates and said doors forming a sauna bath chamber;
   f) air discharge openings formed in said upper body providing communication between said bath chamber and atmosphere; said air discharge openings including at least one door for controlling opening or closing of said communication;
   g) an infrared ray lamp centrally mounted to said upper body on an under surface thereof;
   h) a stereo music amplifier mounted within said chamber of said upper body and in spaced relation to said light lamp;
   i) an air dryer mounted in a recess formed in an inside surface of said back cover plate;
   j) a plurality of exothermic heaters mounted in recesses formed on inside surfaces of said left side cover plate;
   k) a mirror, shower, soap tray and hanger installed on an inside surface of said right side cover plate; and
   l) an instant thermal water machine communicating with said shower, a control box for controlling said lamp, amplifier, dryer and heaters and a stereo cassette, each mounted on an outside surface of one of said left or said right side cover plates.

2. The far infrared rays sauna bathing assembly according to claim 1, wherein each said exothermic heater is a ceramic panel surface exothermic body.

3. The far infrared rays sauna bathing assembly according to claim 1, wherein said shower includes a height control unit.

4. The far infrared rays sauna bathing assembly according to claim 1, wherein said shower produces one of a massaging shower, purifying water shower, jet shower and fog shower.

5. The far infrared rays sauna bathing assembly according to claim 1, wherein a coin inlet timer is installed on one of said left or right side cover plates to allow coin operation of said sauna.

6. A far infrared rays sauna assembly having a small box type prefabricated construction comprising:
   a) a lower body supporting a well, each of said lower body and said well including a drain hole, each said drain hole connected by a drain hose, said lower body including a palette arranged in said well, said palette having a plurality of protrusions on an upper surface thereof, said lower body having a joining part extending along an upper periphery of said lower body;
   b) a front cover plate and a pair of doors;
   c) a left side cover plate and a right side cover plate, each said left side cover plate, said right side cover plate and said back cover plate having a folded lower bottom for connection to said joining part of said lower body using joining nuts;
   d) a plurality of joining bodies for connecting together adjacent edges of each of said back cover plate, left side cover plate and right side cover plate;
   e) an upper body, said upper body forming a chamber and having double wall construction along a lower peripheral edge for attachment to upper edges of at least said back cover plate and said left side and said right side cover plates, said upper body, said lower body, said back cover plate and said left side and said right side cover plates and said doors forming a sauna bath chamber;
   f) air discharge openings formed in said upper body providing communication between said bath chamber and atmosphere; said air discharge openings including at least one door for controlling opening or closing of said communication;
   g) an infrared ray lamp centrally mounted to said upper body on an under surface thereof;

h) a stereo music amplifier mounted within said chamber of said upper body and in spaced relation to said light lamp;
i) an wardrobe mounted in a recess formed in an inside surface of said back cover plate;
j) a plurality of exothermic heaters mounted in recesses formed on inside surface of said left side cover plate;

k) a mirror, shower, soap tray and hanger installed on an inside surface of said right side cover plate; and
l) an instant thermal water machine communicating with said shower, a control box for controlling said lamp, amplifier, dryer and heaters and a stereo cassette, each mounted on an outside surface of one of said left or said right side cover plate.

* * * * *